US00PP19329P2

(12) United States Plant Patent
Kerley et al.

(10) Patent No.: US PP19,329 P2
(45) Date of Patent: Oct. 14, 2008

(54) ***PETUNIA* PLANT NAMED 'KERVERSALM'**

(50) Latin Name: *Petunia×hybrida*
Varietal Denomination: Kerversalm

(76) Inventors: David W. Kerley, Bethany, 49 Station Road, Over, Cambridge CB24 5NJ (GB); Priscilla G. Kerley, Bethany, 49 Station Road, Over, Cambridge CB24 5NJ (GB)

( * ) Notice: Subject to any disclaimer, the term of this patent is extended or adjusted under 35 U.S.C. 154(b) by 0 days.

(21) Appl. No.: 11/978,130

(22) Filed: Oct. 25, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent L Bell
(74) *Attorney, Agent, or Firm*—C. A. Whealy

(57) ABSTRACT

A new and distinct cultivar of *Petunia* plant named 'Kerversalm', characterized by its compact and outwardly spreading growth habit; freely branching habit; early and freely flowering habit; dark salmon pink-colored flowers; and good garden performance.

2 Drawing Sheets

Botanical designation: *Petunia×hybrida.*
Cultivar denomination: 'Kerversalm'.

BACKGROUND OF THE INVENTION

The present invention relates to a new and distinct cultivar of *Petunia,* botanically known as *Petunia×hybrida* and hereinafter referred to by the name 'Kerversalm'.

The new *Petunia* is a product of a planned breeding program conducted by the Inventor in Over, Cambridge, United Kingdom. The objective of the breeding program is to create new *Petunia* cultivars with dark pink-colored flowers.

The new *Petunia* originated from a cross-pollination made by the Inventors on Aug. 15, 2000 in Over, Cambridge, United Kingdom of a proprietary selection of *Petunia× hybrida* identified as code number 00-18-3, not patented, as the female, or seed, parent with a proprietary selection of *Petunia×hybrida* identified as code number 00-66-1, not patented, as the male, or pollen, parent. The new *Petunia* was discovered and selected by the Inventors as a single flowering plant within the progeny of the stated cross-pollination in a controlled environment in Over, Cambridge, United Kingdom on May 31, 2001.

Asexual reproduction of the new *Petunia* by terminal cuttings in a controlled environment in Over, Cambridge, United Kingdom since October, 2001, has shown that the unique features of this new *Petunia* are stable and reproduced true to type in successive generations.

SUMMARY OF THE INVENTION

The cultivar Kerversalm has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Kerversalm'. These characteristics in combination distinguish 'Kerversalm' as a new and distinct cultivar of *Petunia:*

1. Compact and outwardly spreading growth habit.
2. Freely branching habit.
3. Early and freely flowering habit.

4. Dark salmon pink-colored flowers.
5. Good garden performance.

Plants of the new *Petunia* can be compared to plants of the female parent selection. Plants of the new *Petunia* differ from plants of the female parent selection in the following characteristics:

1. Plants of the new *Petunia* have larger flowers than plants of the female parent selection.
2. Plants of the new *Petunia* and the female parent selection differ in flower color as plants of the female parent selection have pale pink-colored flowers.

Plants of the new *Petunia* can be compared to plants of the male parent selection. Plants of the new *Petunia* differ primarily from plants of the male parent selection in the flower color as plants of the male parent selection have light pink-colored flowers with white-colored throats.

Plants of the new *Petunia* can also be compared to plants of the *Petunia* cultivar Kersamfan, disclosed in U.S. Plant Pat. No. 18,128. In side-by-side comparisons conducted in Over, Cambridge, United Kingdom, plants of the new *Petunia* differed from plants of the cultivar Kersamfan in the following characteristics:

1. Plants of the new *Petunia* were more compact and had shorter internodes than plants of the cultivar Kersamfan.
2. Plants of the new *Petunia* were more freely branching and more freely flowering than plants of the cultivar Kersamfan.
3. Plants of the new *Petunia* flowered about three days earlier than plants of the cultivar Kersamfan.
4. Plants of the new *Petunia* had smaller flowers than plants of the cultivar Kersamfan.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanical description which accurately describe the colors of the new *Petunia.*

The photograph on the first sheet comprises a side perspective view of a typical plant of 'Kerversalm' grown in a container.

The photograph on the second sheet is a close-up view of a typical flower of 'Kerversalm'.

DETAILED BOTANICAL DESCRIPTION

The photograph and following observations, measurements and values describe plants grown in Over, Cambridge, United Kingdom, under commercial practice during the summer in a glass-covered greenhouse with day temperatures ranging from 18° C. to 28° C., night temperatures ranging from 14° C. to 20° C. and light levels averaging 50 kilolux. Rooted young plants had been growing for about ten weeks when the photographs and description were taken. Plants were pinched one time before planting. In the following description, color references are made to The Royal Horticultural Society Colour Chart, 1995 Edition, except where general terms of ordinary dictionary significance are used.

Botanical classification: *Petunia×hybrida* cultivar Kerversalm.

Parentage:

*Female, or seed, parent.*—Proprietary selection of *Petunia×hybrida* identified as code number 00-18-3, not patented.

*Male, or pollen, parent.*—Proprietary selection of *Petunia×hybrida* identified as code number 00-66-1, not patented.

Propagation:

*Type.*—By terminal cuttings.

*Time to initiate roots, summer.*—About ten days at temperatures of 21° C.

*Time to initiate roots, winter.*—About two weeks at temperatures of 21° C.

*Time to produce a rooted young plant, summer.*—About 30 days at temperatures of 20° C.

*Time to produce a rooted young plant, winter.*—About 45 days at temperatures of 20° C.

*Root description.*—Fine, fibrous; white in color.

*Rooting habit.*—Freely branching; dense.

Plant description:

*Plant and growth habit.*—Compact and outwardly spreading growth habit. Freely branching habit with about eight lateral branches developing per plant. Moderately vigorous growth habit.

*Plant height.*—About 30 cm.

*Plant diameter.*—About 60 cm.

Lateral branch description:

*Length.*—About 27 cm.

*Diameter.*—About 3.25 mm.

*Internode length.*—About 3 cm.

*Aspect.*—Initially upright to outwardly spreading.

*Texture.*—Pubescent.

*Color.*—144A.

Foliage description:

*Arrangement.*—Before flowering, alternate, simple; after flowering, opposite, simple.

*Length.*—About 4.2 cm.

*Width.*—About 2.8 cm.

*Shape.*—Elliptic.

*Apex.*—Acute.

*Base.*—Attenuate.

*Margin.*—Entire; slightly undulate.

*Texture, upper and lower surfaces.*—Pubescent.

*Venation pattern.*—Pinnate; arcuate.

*Color.*—Developing foliage, upper surface: 137B to 137C. Developing foliage, lower surface: 147B. Fully expanded foliage, upper surface: 137A; venation, 144A. Fully expanded foliage, lower surface: 147B; venation, 144B.

*Petiole length.*—About 4 mm.

*Petiole diameter.*—About 2 mm.

*Petiole texture, upper and lower surfaces.*—Pubescent.

*Petiole color, upper surface.*—144A to 144B.

*Petiole color, lower surface.*—144A.

Flower description:

*Flower arrangement and habit.*—Single-type salverform flowers; singly arising from leaf axils. Freely flowering habit with usually about 205 developing per plant. Flowers persistent. Flowers face mostly outwardly.

*Fragrance.*—None detected.

*Natural flowering season.*—Plants flower continuously during the summer in the United Kingdom. Early flowering habit, plants typically beginning flowering about seven weeks after planting.

*Flower longevity.*—Individual flowers last about four days on the plant.

*Flower diameter.*—About 4.4 cm.

*Flower depth (height).*—About 4.5 cm.

*Flower throat diameter.*—About 1.5 cm.

*Flower tube length.*—About 2.7 cm.

*Flower tube diameter (base).*—About 2.5 mm.

*Flower bud.*—Shape: Ovoid. Length: About 3.9 cm. Diameter: About 6.5 mm. Color: Towards the apex, between 70A and 70C; towards the base, 145A.

*Corolla.*—Arrangement: Five petals fused at the base and opening into a flared trumpet. Petal length from throat: About 2.7 cm to 3.5 cm. Petal lobe width: About 3.1 cm to 3.4 cm. Petal shape: Spatulate. Petal apex: Obtuse, slightly undulate. Petal margin: Entire; slightly undulate. Petal texture, upper surface: Smooth, glabrous. Petal texture, lower surface: Slightly pubescent. Throat texture: Smooth, glabrous. Tube texture: Pubescent. Color: Petals, when opening, upper surface: 58B to 58C. Petals, when opening, lower surface: 54B. Petals, fully opened, upper surface: 55A; color becoming closer to 55B with development; at base and venation, 58B. Petals, fully opened, lower surface: 55B; venation, 55B. Flower throat: 56D; venation, 56D. Flower tube: 56D; venation, 56D.

*Calyx.*—Arrangement: One star-shaped calyx tube with five sepals fused at the base per flower. Sepal length: About 2.2 cm. Sepal width: About 4.7 mm. Sepal shape: Narrowly oblong. Sepal apex: Obtuse. Sepal margin: Entire. Sepal texture, upper and lower surfaces: Pubescent. Color, immature and mature, upper surface: 147A to 147B. Color, immature and mature, lower surface: 137A to 137B.

*Peduncles.*—Length: About 3.4 cm. Diameter: About 2 mm. Strength: Strong. Texture: Pubescent. Color: 144A.

*Reproductive organs.*—Stamens: Quantity: About five per flower. Anther shape: Ovate. Anther length: About 3 mm. Anther color: 4D. Pollen amount: Abundant. Pollen color: 155D. Pistils: Quantity: One per flower. Pistil length: About 1.9 cm. Style length: About 1.7 cm. Style color: 145B. Stigma shape: Oval. Stigma color: Between 144A and 144D. Ovary color: 144A.

*Seed/fruit.*—Seed and fruit development have not been observed on plants of the new *Petunia*.

Garden performance: Plants of the new *Petunia* have been observed to have good garden performance and tolerate wind, rain and temperatures ranging from about 1° C. to about 40° C.

Pathogen/pest resistance: Plants of the new *Petunia* have not been observed to be resistant to pathogens and pests common to *Petunia*.

It is claimed:

1. A new and distinct *Petunia* plant named 'Kerversalm' as illustrated and described.

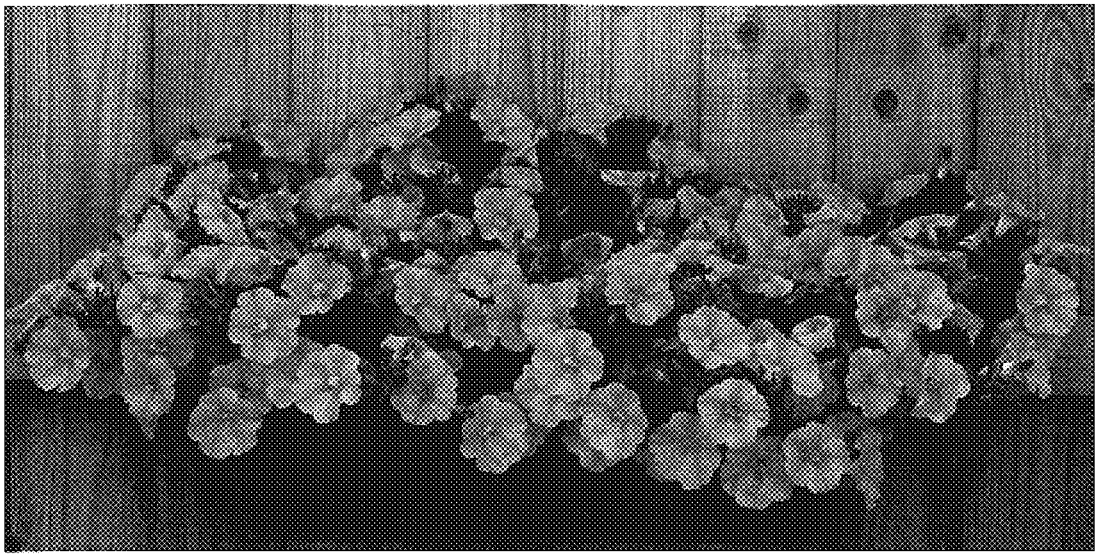

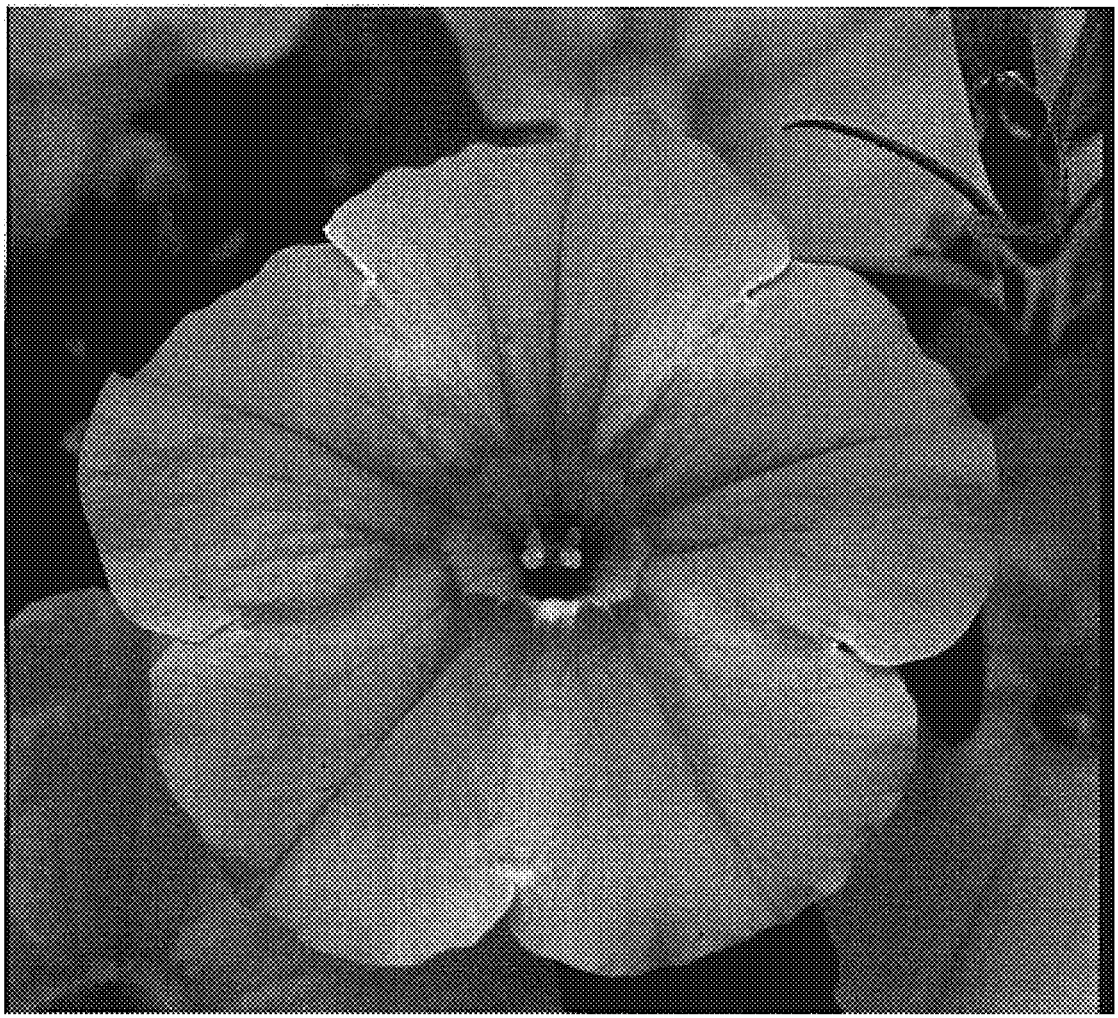

* * * * *